United States Patent [19]

Simonnet

[11] Patent Number: 6,022,559

[45] Date of Patent: Feb. 8, 2000

[54] AQUEOUS DISPERSION OF DEHYDRATION-RESISTANT VESICLES

[75] Inventor: Jean-Thierry Simonnet, Paris, France

[73] Assignee: L'Oreal, Paris, France

[21] Appl. No.: 08/978,377

[22] Filed: Nov. 25, 1997

[30] Foreign Application Priority Data

Nov. 28, 1996 [FR] France .................................. 96 14602

[51] Int. Cl.⁷ ............................ A61K 9/127; A61K 6/00; A61K 7/06
[52] U.S. Cl. ......................... 424/450; 424/401; 424/455; 424/461; 424/70.1; 424/70.11; 424/70.12; 424/70.13; 424/70.15; 424/70.16; 424/70.21; 424/70.22
[58] Field of Search ...................... 424/401, 450, 424/455, 461, 70.1, 70.2, 70.11, 70.12, 70.13, 70.15, 70.16, 70.21, 70.22

[56] References Cited

U.S. PATENT DOCUMENTS

| | | | |
|---|---|---|---|
| 4,240,450 | 12/1980 | Grollier et al. | 132/7 |
| 4,830,857 | 5/1989 | Handjani et al. | 424/450 |
| 5,174,930 | 12/1992 | Stainmesse et al. | 264/4.6 |
| 5,741,518 | 4/1998 | Ribier et al. | 424/450 |

FOREIGN PATENT DOCUMENTS

| | | |
|---|---|---|
| 43 02 132 | 1/1994 | Germany . |
| 2 013 609 | 8/1979 | United Kingdom . |
| 91 15947 | 10/1991 | WIPO . |

*Primary Examiner*—Thurman K. Page
*Assistant Examiner*—Lakshmi Channavajjale
*Attorney, Agent, or Firm*—Nixon & Vanderhye P.C.

[57] ABSTRACT

A dispersion, in an aqueous medium, of dehydration-resistant vesicles containing a lipid phase and an encapsulated aqueous phase. The dispersion additionally contains, either in the aqueous medium or in the encapsulated aqueous phase or in both, at least one polymer, in the form of particles, which has a glass transition temperature Tg, in the presence or absence of a plasticizing agent, of lower than 70° C. at 0% relative humidity. The dispersion can be used in the cosmetic or pharmaceutical fields for topical application for the care and/or makeup of the skin and for care of the scalp and/or hair.

24 Claims, No Drawings

AQUEOUS DISPERSION OF DEHYDRATION-RESISTANT VESICLES

The present invention relates to an aqueous dispersion of dehydration-resistant vesicles and of polymer particles, and to a cosmetic or pharmaceutical composition for topical application, based on such a dispersion, the said composition being intended especially for the cosmetic or dermatological treatment of the skin.

"Vesicle" is intended, according to the invention, to mean any particulate structure including, on the one hand, a membrane or "lipid phase" consisting of one or a number of concentric leaflets, these leaflets comprising one or a number of bimolecular layers based on ionic or nonionic amphiphilic lipids and, on the other hand, an aqueous phase encapsulated by this lipid phase. Within the meaning of the invention liposomes and niosomes constitute especially such vesicles.

The membrane structure of the vesicles, such as that of liposomes or of niosomes, in aqueous dispersion, is particularly sensitive to any dehydration phenomenon, that is to say any phenomenon entailing a possibly complete elimination of the aqueous medium from the dispersion. In practice this can result in an undesirable, because premature, release of a product conveyed by the vesicles.

This problem of dehydration resistance of the vesicles in aqueous dispersion arises very particularly during a topical application of a vesicular dispersion. It is found, in fact, in this case that the vesicles are not only subjected to violent shearing but also to a dehydration resulting, as has been demonstrated by studies of cryofracture on human skin in vitro, in an at least partial collapse of the vesicles, a fusion with formation of a multilamellar film at the surface of application and, consequently, a premature release of the conveyed product.

It is known to protect vesicles from the effects of the dehydration produced by freeze-drying, which is nowadays a conventional technique for storing vesicles, by addition, to the aqueous dispersion of vesicles, before freeze-drying, of a high content of a cryoprotective agent (approximately 15 to 30% by weight) such as sucrose or trehalose. While these agents are recognized as being efficient, their presence in a cosmetic or pharmaceutical composition for topical application nevertheless raises some problems because of their high content in the composition, which in particular restricts the cosmetic or pharmaceutical effectiveness of a given quantity of the composition employed, and which also gives it a more or less adhesive character which is quite unacceptable to the user on a topical application.

Other means making it possible to improve the dehydration resistance of vesicles in aqueous dispersion have therefore been searched for.

It has now been discovered quite surprisingly and unexpectedly that it is possible to make vesicles in aqueous dispersion substantially more resistant to dehydration, especially during a topical application, by adding a polymer in dispersion either in the aqueous medium of the dispersed vesicles or in the aqueous phase of the vesicles or in both at the same time.

The expression "polymer in dispersion" is intended according to the invention to mean a polymer in the form of generally spherical particles which are dispersed in an appropriate aqueous medium.

The subject matter of the present invention is therefore a dispersion, in an aqueous medium, of dehydration-resistant vesicles consisting of a lipid phase and of an encapsulated aqueous phase, characterized in that it additionally contains, either in the said aqueous medium or in the said encapsulated aqueous phase, or in both at the same time, at least one polymer in dispersion in the form of particles, the said polymer being selected from the group consisting of the polymers which have a glass transition temperature Tg, in the presence or absence of a plasticizing agent, lower than 70° C. at 0% relative humidity or lower than 55° C. at 65% relative humidity.

The polymer employed in dispersion according to the invention must exhibit a glass transition temperature Tg corresponding to the conditions described above. It has in fact been found, surprisingly and unexpectedly, that only the polymers which have a Tg, in the presence or absence of a plasticizing agent, lower than 70° C. at 0% relative humidity or lower than 55° C. at 65% relative humidity make it possible to improve the dehydration resistance of vesicles in dispersion.

The glass transition temperature Tg of a given polymer, in the presence or absence of a plasticizing agent, is measured in a known manner by differential thermal analysis.

The preferred polymers in dispersion according to the invention are those whose particles are sufficiently stable in the dispersed state in the aqueous medium, thus avoiding the presence of a stabilizing agent such as a surfactant, a hydrophilic stabilizing agent, a protective colloid polymer or a mixture of these. In fact, a person skilled in the art will understand that the presence of a stabilizing agent is in most cases incompatible with the amphiphilic nature of the lipids predominantly forming the lipid phase or membrane of the vesicles in the dispersion of the invention. The absence of any surfactant or other stabilizing agent is therefore quite a significant advantage during a topical application of a cosmetic or pharmaceutical composition, because of their irritant nature.

On account of the above, the polymers which can be employed as polymer in dispersion according to the invention can be selected from synthetic polymers, polymers of natural origin and mixtures thereof.

1. Synthetic Polymers

Among synthetic polymers there may be mentioned especially polyesters, polyurethanes, polymers containing carboxylic acid functional groups and vinyl polymers.

1.1. The polyesters which can be employed in the dispersion according to the invention can be obtained, in a known manner, by polycondensation of aliphatic or aromatic dicarboxylic acids with aliphatic or aromatic diols or polyols. As aliphatic dicarboxylic acids there may be mentioned succinic acid, glutaric acid, adipic acid, pimelic acid, suberic acid or sebacic acid. As aromatic dicarboxylic acids there may be mentioned terephthalic acid or isophthalic acid or a derivative thereof such as phthalic anhydride. As aliphatic diols there may be mentioned ethylene glycol, propylene glycol, diethylene glycol, neopentyl glycol, cyclohexanedimethanol and 4,4'-(1-methylpropylidene)bisphenol. As polyols there may be mentioned glycerol, pentaerythritol, sorbitol and dimethylolpropane.

Polyesters which can be employed in the dispersion according to the invention are understood to mean also polyester amides, polyesters with a fatty chain and epoxy ester resins. The polyester amides can be obtained similarly to the polyesters, but the polycondensation also involves a diamine and/or an amino alcohol. Ethylenediamine, hexamethylenediamine and meta- or para-phenylenediamine may be mentioned as diamine. Monoethanolamine may be mentioned as aminoalcohol. The polyesters with a fatty chain can be obtained by the use of fatty chain diols during the polycondensation. The epoxy ester resins can be obtained by polycondensation of fatty acids with a condensate containing α,γ-diepoxy ends.

The polyesters as defined above may advantageously include units carrying anionic groups, among which there may be mentioned those derived from dimethylolpropionic acid, trimellitic acid or a derivative thereof, such as trimellitic anhydride, or a difunctional dicarboxylic sulphoaryl compound substituted on the aromatic ring by a —SO$_3$M group in which M denotes a hydrogen atom or a metal ion such as Na$^+$, Li$^+$ or K$^+$, like, for example, the sodium salt of 3-sulphopentanediol acid and the sodium salt of 5-sulpho-1,3-benzenedicarboxylic acid.

Among the polyesters which can be applied in the dispersion according to the invention there may be mentioned more particularly polyesters and polyester amides including units derived from a difunctional dicarboxylic sulphoaryl compound as described above. Such polyesters and polyester amides are known and are described especially in U.S. Pat. No. 3,779,993, U.S. Pat. No. 4,300,581 and EP-0540374.

According to a particular embodiment of the dispersion according to the invention the polymer is selected from polyesters containing sulphonic groups, that is to say polyesters including at least units derived from isophthalic acid, salts of sulphoaryl dicarboxylic acid and from diethyleneglycol. Among these there may be mentioned particularly the polyesters including units of isophthalic acid, of the sodium salt of sulphoisophthalic acid, of diethylene glycol and of 1,4-cyclohexanedimethanol, such as those marketed under the names of "AQ29®", "AQ38®", "AQ48 ultra®", "AQ1350®", "AQ1045®", "AQ1950®" and "AQ14000®" by Eastman Chemical. These polyesters may additionally contain units derived from ethylene glycol, from tri- and tetraethylene glycol and from terephthalate, such as those marketed under the names "Polycare PS 20®", "Polycare PS30®" and "Polycare PS 32®" by Rhône-Poulenc.

Among the polyesters which can be employed in the dispersion according to the invention there may also be mentioned particularly the polyesters containing a terminal amine functional group which are neutralized, for example, with lactic acid, such as that marketed under the name of "Lexamer C120 lactate®" by Inolex, and the polyester block copolymers of the type of phthalic and sulphophthalic acid/ethylene glycol/polymethylsiloxane α,γ-hydroxypropyl, such as that marketed under the name "PEJ 549®" by Rhône-Poulenc.

1.2. The polyurethanes which can be employed in dispersion according to the invention may be anionic, cationic, nonionic or amphoteric. They may be selected especially from acrylic polyurethanes, polyurethane-polyvinylpyrrolidones, polyether-polyurethanes, polyureas, polyester-polyurethanes and mixtures thereof.

In particular the polyester-polyurethanes are especially those described in FR-A-2708615.

1.3. The polymers containing carboxylic acid functional groups which can be employed in dispersion according to the invention are especially those in which the carboxylic acid functional groups are partially neutralized with a neutralizing agent in order to provide the polymer particles with a sufficiently water-insoluble character.

The partial neutralization of the polymers containing carboxylic acid functional groups makes it possible furthermore to obtain advantageously polymers in dispersion which are particularly stable in the absence of a hydrophilic stabilizer or of surfactant or else of protective colloid.

The neutralizing agent is preferably either a diamine or the association of a salt of a polyvalent metal and of an organic or inorganic base. The diamines are selected from lysine, arginine or cystine. The polyvalent metal salts are selected from calcium, zinc, magnesium, barium, aluminium and zirconium bromides, chlorides, nitrates, acetates, carbonates and sulphates, and the inorganic or organic bases are selected, for example, from sodium hydroxide, potassium hydroxide or aqueous ammonia or from an aminoalcohol such as 2-amino-2-methyl-1-propanol (AMP), triethanolamine, triisopropanolamine (TIPA), monoethanolamine, diethanolamine, tri[(2-hydroxy)-1-propyl]amine, 2-amino-2-methyl-1,3-propanediol (AMPD) and 2-amino-2-hydroxymethyl-1,3-propanediol, as well as optionally from diamines such as those mentioned above.

It is obvious that the upper limit degree of neutralization which it would be appropriate not to exceed in order that the polymer containing carboxylic acid functional groups should remain insoluble in water will be a function of the nature of each polymer containing carboxylic acid functional groups and of the neutralizing agent. In general, when the neutralizing agent is a diamine, the degree of neutralization is generally between 30 and 80% and preferably between 40 and 70% if the polymer has less than 2 meq/g of carboxylic acid functional groups and between 10 and 50%, preferably between 10 and 40% if the polymer has more than 2 meq/g of carboxylic acid functional groups.

If the neutralizing agent is an association of a salt of polyvalent metal and of an organic or inorganic base, the polymer is first neutralized with the polyvalent metal salt to a degree of between 4 and 20%, preferably between 4 and 10%, and is then coneutralized with the inorganic or organic base to a degree of total neutralization of between 30 and 80%, preferably between 40 and 70% if the polymer has less than 2 meq/g of carboxylic acid functional groups and between 10 and 50%, preferably between 10 and 40%, if the polymer has more than 2 meq/g of carboxylic acid functional groups.

These polymers containing carboxylic acid functional groups, employed in dispersion according to the invention, are especially film-forming polymers commonly employed for producing cosmetic compositions for hairsetting, among which there may be mentioned more particularly:

(i) polyoxyethylenated vinyl acetate/crotonic acid copolymers such as that marketed under the name of "Aristoflex A®", acid value 56, by Hoechst, (ii) vinyl acetate/crotonic acid copolymers such as that marketed under the name of "Luviset CA66®", of acid value 65, by BASF, (iii) vinyl acetate/crotonic acid/vinyl neodecanoate terpolymers such as that marketed under the name of "Resin 28-29-30®", of acid value 65, by National Starch, (iv) N-octylacrylamide/methyl methacrylate/hydroxypropyl methacrylate/acrylic acid/tert-butylaminoethyl methacrylate copolymers, such as that marketed under the name of "Amphornerk®", of acid value 137, by National Starch, (v) methyl vinyl ether/maleic anhydride alternating copolymers monoesterified with butanol, such as that marketed under the name of "Gantrez ES 425®", of acid value 260, by GAF, (vi) acrylic acid/ethyl acrylate/N-tert-butylacrylamide terpolymers such as that marketed under the name of "Ultrahold 8®", of acid value 62, by BASF, and (vii) the polymers corresponding to the following general formula:

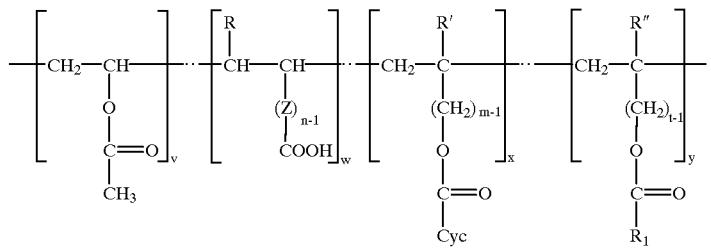

in which:
R, R' and R", which are identical or different, denote a hydrogen atom or a methyl radical,
m, n and t are 1 or 2,
$R_1$ denotes a saturated or unsaturated, linear or branched alkyl radical containing from 2 to 21 carbon atoms,
Z denotes a divalent radical taken from the group consisting of: —$CH_2$—, —$CH_2$—O—$CH_2$— and —$CH$,—O-$(CH_2)_2$—,
Cyc denotes a radical chosen from:
(a) a radical of formula:

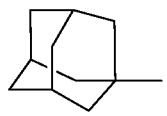

(b) a radical of formula:

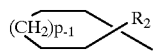

in which:
$R_2$ denotes a hydrogen atom or a methyl radical, and p is 1 or 2
(c) a radical of formula:

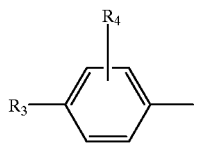

in which:
$R_3$ denotes a hydrogen atom, a methyl, ethyl, tert-butyl, ethoxy, butoxy or dodecyloxy radical and $R_4$ denotes a hydrogen atom, an alkyl radical of 1 to 4 carbon atoms or an alkoxy radical of 1 to 4 carbon atoms,
and (d) a radical of formula:

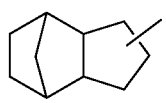

v denotes from 10 to 91% and preferably from 36 to 84% by weight,
w denotes from 3 to 20% and preferably from 6 to 12% by weight,
x denotes from 4 to 60% and preferably from 6 to 40% by weight,
and y denotes from 0 to 40% and preferably from 4 to 30% by weight,
v+w+x+y being equal to 100%.

Among these polymers there may be mentioned especially the vinyl acetate/vinyl 4-tert-butyl benzoate/crotonic acid (65/25/10) copolymer 50% neutralized with lysine and the vinyl acetate/crotonic acid/vinyl 4-tert-butyl benzoate (65/10/25) copolymer 60% neutralized with lysine.

1.4. The vinyl polymers which can be employed in dispersion according to the invention may result from the homopolymerization or copolymerization of monomers selected from vinyl esters, styrene or butadiene. As examples of vinyl esters there may be mentioned vinyl acetate, vinyl neodecanoate, vinyl pivalate, vinyl benzoate and vinyl 4-tert-butyl benzoate.

2. Natural Polymners

Among the polymers of natural origin which can be employed in dispersion according to the invention there may be mentioned shellac resin, sandarac gum, dammars, elemis, copals, cellulose derivatives and mixtures thereof.

In particular, the cellulose derivatives may be selected from cellulose ethers, nonionic cellulose esters and anionic cellulose esters containing carboxylic acid functional groups, the said carboxylic acid functional groups being neutralized to a degree of neutralization of between 10 and 80% with the aid of a neutralizing agent as described above in the case of synthetic polymers containing carboxylic acid functional groups.

Among the cellulose ethers which are insoluble in water there may be mentioned especially ethyl celluloses and in particular those marketed under the names of "Ethocel®" by Dow Chemical.

Among the water-insoluble, nonionic cellulose esters there may be mentioned especially cellulose acetates, cellulose propionates, cellulose butyrates, cellulose acetopropionates and cellulose acetobutyrates.

Finally, among the water-insoluble anionic cellulose esters containing carboxylic acid functional groups there may be mentioned especially cellulose acetophthalate, cellulose acetate succinate, cellulose propionate succinate, cellulose butyrate succinate, cellulose acetopropionate succinate, cellulose acetobutyrate succinate, cellulose acetate trimellitate, cellulose butyrate trimellitate, cellulose propionate trimellitate, cellulose acetopropionate trimellitate and cellulose acetobutyrate trimellitate.

The polymer which can be employed in the dispersion according to the invention may include in a known manner a plasticizing agent in order especially to control the glass transition temperature Tg of the polymer, which must correspond to the abovementioned conditions. The quantity of plasticizing agent is chosen by a person skilled in the art on the basis of his/her general knowledge, so as to obtain an appropriate polymer system.

Among the plasticizing agents which can be employed there may be mentioned:

"Carbitols®" from Union Carbide, namely "Carbitol" or diethylone glycol ethyl ether, "imethyl Carbitol" or diethylenc glycol methyl ether, "butyl Carbitol" or diethylene glycol butyl ether or else "hexyl Carbitol" or diethylene glycol hexyl ether, "Cellosolves®" from Union Carbide, namely "Cellosolve" or ethylene glycol ethyl ether, "butyl Cellosolve" or ethylene glycol butyl ether, "hexyl Cellosolve" or ethylene glycol hexyl ether, propylene glycol derivatives and in particular propylene glycol phenyl ether, propylene glycol diacetate, dipropylene glycol butyl ether, tripropylene glycol butyl ether, as well as "Dowanols®" from Dow Chemical, namely "Dowanol PM®" or propylene glycol methyl ether, "Dowanol DPM®" or dipropylene glycol methyl ether and "Dowanol TPM®" or tripropylene glycol methyl ether.

There may also be mentioned:

diethylene glycol methyl ether or "Dowanol DM®" from Dow Chemical, castor oil oxyethylenated with 40 moles of ethylene oxide, such as that sold by Rhône-Poulenc under the name of "Mulgofen EL-719®", benzyl alcohol, triethyl citrate sold by Pfizer under the name of "Citroflex-2®", 1,3-butylene glycol, diethyl, dibutyl and diisopropyl phthalates and adipates, diethyl and dibutyl tartrates, diethyl, dibutyl and di-2-ethylhexyl phosphates, and glycerol esters such as glycerol diacetate (diacetin) and glycerol triacetate (triacetin).

A plasticizing agent selected from the group consisting of dipropylene glycol methyl ether, tripropylene glycol methyl ether, diethyl adipate, diisopropyl adipate and glycerol triacetate is preferably employed.

The polymer in dispersion, that is to say the dispersion of polymer particles in an appropriate aqueous medium, is prepared either by polymerization of the corresponding monomer(s) in an appropriate aqueous medium (which is then referred to as latex or synthetic latex), or from a polymer in an appropriate aqueous medium (which is then referred to as pseudolatex).

According to a preferred embodiment of the present invention the polymer in dispersion is prepared by dispersing a polymer in an appropriate aqueous medium (pseudolatex). This preparation process consists in dissolving the water-insoluble polymer in an organic solvent which is soluble or partially soluble in water, in dispersing, with stirring, the solution thus obtained in the appropriate aqueous medium and in then proceeding to remove the organic solvent by vacuum evaporation. The water-insoluble polymer can also be dispersed in water at a temperature above its glass transition temperature Tg without addition of any particular solvent.

The particles of the polymer in dispersion which is thus obtained preferably have a mean size of between 5 and 2000 nm arid more preferably between 10 and 500 nm.

The appropriate aqueous medium for the preparation of the polymer in dispersion may be water and any other aqueous solution.

The aqueous dispersion of vesicles forming the subject-matter of the invention can be prepared according to two alternative forms, namely either by simply mixing a polymer in dispersion with an aqueous dispersion of vesicles which has already formed, or by mixing a lipid phase with a polymer in dispersion, whose aqueous medium causes the formation of the vesicle dispersion. It will be understood that it is thus possible to obtain, according to the first alternative form, a dispersion of vesicles in which the external aqueous medium of dispersion alone contains polymer particles in dispersion and, according to the second alternative form, a dispersion in an aqueous medium of vesicles in which the aqueous medium of dispersion and the encapsulated aqueous phase of the vesicles contain particles of polymer in dispersion.

Whichever the alternative form employed for the formation of the dispersion which is the subject-matter of the invention, the lipid phase of the vesicles which is used is the substances generally employed for the preparation of the liposomes and niosomes as described, for example, in the paper by Bangham, Standish & Watkins, J. Mol. Biol. 13, 238 (1965) and in FR-A-2315991, FR-A-2694884 or FR-A-2714596.

Thus, besides the known ionic or nonionic amphiphilic lipid compounds, mixed or otherwise, the lipid phase of the vesicles may also include, in a known manner, at least one additive whose chief function is to lower the permeability of the vesicles, to prevent their fusion and to increase the encapsulation ratio.

This additive is generally preferably selected from the group consisting of sterols (phytosterol, cholesterol, polyoxyetliylenated phytosterol), monoalcohols, diols and triols with a long chain (phytanetriol).

The lipid phase may also contain, in a known manner, at least one additive whose chief function is to prevent the flocculation of the vesicles obtained. In general this additive is preferably selected from the group consisting of long-chain amines and their quaternary ammonium derivatives, phosphoric esters of a fatty alcohol and their alkali metal (sodium, potassium) salts, such as dicetyl phosphate, sodium dicetyl phosphate, alkyl sulphates (sodium cetyl sulphate), alkali metal salts of cholesterol sulphate or of cholesterol phosphate, the sodium salt of phosphatidic acid, lipoaminoacids and their salts such as sodium acylglutamates (such as the monosodium and disodium salts of N-stearoylglutamic acid which are marketed under the names of "Acylglutamate HS 11®" and "Acylglutamate HS 21®" respectively by Ajinomoto).

From the lipid phase described above the vesicles of the dispersion are prepared by any known process and more particularly by the so-called process "by combined melting of the lipids", which enables them to be prepared in a simple manner on industrial scale. This process consists essentially, in a first step, in mixing the various lipids and optional additives of the lipid phase, by melting and with stirring and, in a second step, in mixing the lipid phase obtained, with heating and with rapid stirring, with an appropriate aqueous medium constituting the aqueous phase to be encapsulated, while maintaining the stirring for a sufficient time. According to the first alternative form of the process the aqueous medium may be water or any other aqueous solution and, according to the second alternative form, the aqueous medium is that of the polymer in dispersion which is employed as described above.

The size of the vesicles in dispersion which are thus obtained may optionally be homogenized, for example by passing the vesicle dispersion through a high-pressure homogenizer, at ambient temperature, or through an ultrasonic device.

The mean size of the vesicles thus obtained in dispersion is preferably between 10 and 5000 nm and preferably between 50 and 1000 nm.

The concentration of the polymer in the dispersion according to the invention is expressed as a percentage by weight of polymer, optionally plasticized, relative to the total weigh, of the dispersion according to the invention.

This polymer concentration is preferably between 0.01 and 30% and preferably between 0.01 and 5%.

The concentration of the vesicles or "vesicle concentration" in the dispersion according to the invention is expressed as a percentage by weight of lipid phase, as defined above relative to the total weight of the dispersion according to the invention.

This vesicle concentration is preferably between 0.1 and 30%, and more preferably between 0.5 and 10%.

According to a preferred embodiment of the present invention the weight ratio of the polymer, in the form of particles in dispersion, to the lipid phase is between 1:500 and 20:1 and preferably between 1:100 and 1:1.

The resistance to dehydration of the vesicles in the dispersions according to the invention has been tested with regard to an extreme situation of dehydration of the vesicles, namely that generated by a freeze-drying operation.

This freeze-drying test was performed in the following conditions: a lipid phase was employed composed of: polyethylene glycol 400 stearate/cholesterol/"Acylglutamate HS 21®" (disodium salt of N-stearoylglutamic acid, marketed by Ajinomoto) in proportions of 45/45/10. The vesicle concentration adopted was 3% by weight of lipid phase relative to the total weight of the final dispersion. The polymer concentration employed was 0.3% by weight of polymer relative to the weight of the final dispersion. The dispersions thus obtained were next subjected to a conventional freeze-drying operation: each of them was first frozen on the walls of a round bottom flask rotating in liquid nitrogen, the frozen dispersion having then been placed in freeze-drier, thus to obtain, after a sufficient period of sublimation of the aqueous dispersion medium, a pasty product of white colour, which can be stored as freeze-dried material. A vesicle dispersion was obtained anew by rehydration of the freeze-dried material with the same aqueous dispersion medium employed previously for the preparation of the dispersion.

For each of the dispersion thus formed, the freeze-drying tEest first of all consisted in verifying that there was no recrystallization of some lipids of the lipid phase of the vesicles (in particular of cholesterol) and that the vesicle dispersion after rehydration was fine and homogeneous according to a visual check.

When these first conditions were fulfilled, a particle size measurement of the vesicles was performed next, the result of which was compared with that of a measurement performed before the freeze-drying operation. It was considered that a positive result was obtained if the mean size of thovesicles after freeze-drying was not more than twice that before freeze-drying.

Dispersions according to the invention, each of which included one of the following polymers, were thus tested in the conditions described above:

polyesters containing sulphonic groups "AQ29®" and "AQ38®", marketed by Eastman Chemical and "Polycare PS 20®" and "Poly(,are PS $_{32}$®", marketed by Rhône-Poulenc;

neutralized polyester containing end amine functional groups "Lexamer C120 lactate®" marketed by Inolex; polyester "PEJ549®" marketed by Rhône-Poulenc;

vinyl acetate/vinyl butyl benzoate/crotonic acid copolymer in the proportions (65/25/10) 50% neutralized with lysine and including tripropylene glycol methyl ether in a proportion of 10% by weight as plasticizing agent.

Each of these polymers was employed in the form of a dispersion added, on the one hand, to a vesicles dispersion already formed (first alternative form) and added, on the other hand, to a lipid phase as described above (second alternative form).

The results of particle size measurements before/after freeze-drying have made it possible to ascertain a wholly positive result for each of the dispersions according to the invention which were tested, regardless of the alternative process form employed for preparing it. On the other hand, the test of a control dispersion made up only of vesicles in dispersion, which were obtained from the same lipid phase, did not produce any positive result (massive recrystallization of the cholesterol and large-sized residual vesicles)

Furthermore, the carrier effect through the skin of a dispersion according to the invention applied topically was tested in the case of a compound contained in the vesicles, in the following conditions.

A dispersion according to the invention was formed including, relative to the total weight of the dispersion, 5% by weight of lipid phase, 0.5% by weight of polymer (i.e. weight ratio of polymer to the lipid phase of 1:10) and 0.3% by weight of a compound which can be detected by the EPR or "EPR probe" technique, present in the vesicles.

The composition of the lipid phase was: polyethylene glycol 400 stearate/cholesterol/"Acylglutamate HS 21®" in the proportions 45/45/10. The polymer in dispersion was the polymer containing sulphonic groups "AQ38®" marketed by Eastman Chemical. The EPR probe was ASL (N-(1-oxyl-,2,6,6-tetramethyl-4-piperidyl)-N-dimethyl-N-hydroxyethylammonium iodide), which has the formula:

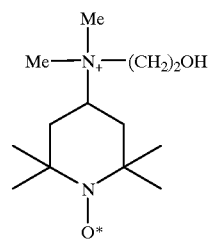

This dispersion according to the invention was prepared by first forming, in a known manner, an aqueous dispersion of vesicles from the lipid phase and from an aqueous solution of demineralized water containing the EPR probe, the latter being thus encapsulated in the vesicles of the dispersion formed.

This dispersion of vesicles was next mixed with the polymer in the form of particles in dispersion in demineralized water (first alternative form).

Table I below gives, for the dispersion according to the invention thus prepared, the diffusion coefficient D of the ASL probe in the stratum corneum and in the epidermis/dermis, as well as the penetration $_A$L 25-5.

The measurements of the diffusion coefficient D and of the penetration $_A$L 25-5 were performed by a combination of two methods employing a paramagnetic probe: on the one hand, unidimensional and periodic electron paramagnetic resonance (EPR) and, on the other hand, EPR kinetic imaging. These two methods are described respectively in the papers in the Internatinal Journal of Pharmaceutics, 62

(1990), pages 75–79, Elsevier by V. Cabrijelcic et al. "Evaluation of liposomes as drug carriers into the skin by one-dimensional EPR imaging" and in Periodicum Biologorum, Vol. 93, No. 2, pages 245–246 (1991) by V. Gabrijelcic et al. "Liposome entrapped molecules penetration into the skin measured by nitroxide reduction kinetic imaging".

Each of the methods was carried out four times.

TABLE I

| EPR measurements | ASL probe alone | Control vesicles dispersion | Dispersion according to the invention: control dispersion + polymer "AQ38 ®" in dispersion |
|---|---|---|---|
| Diffusion coefficient D: (×10$^{7;}$ in cm$^2$/s) | | | |
| stratum corneum | 1.0 | 41.6 | 58 |
| epidermis/dermis | 4.2 | 33 | 33 |
| Penetration $_\Delta$L 25-5 | 0.00 | 0.12 ± 0.01 | 0.17 ± 0.02 |

From Table I above it follows that the value of the coefficient D of diffusion of the ASL probe into the stratum corneum in the control dispersion, that is to say without the presence of the polymer in dispersion, is increased by more than 39% when this same ASL probe is encapsulated in the vesicles of the dispersion according to the invention.

Furthermore, the value of the penetration $_\Delta$L 25-5 of the ASL probe encapsulated in the control dispersion is increased by more than 40% when this same ASL probe is encapsulated in the vesicles of the dispersion according to the invention.

Comparable results have been obtained with a dispersion according to the invention including the same components but prepared according to the second alternative form as described above (particles of polymer also present in the encapsulated aqueous phase of the vesicles).

These results can be explained by an improved resistance to dehydration during the application of the dispersion onto the skin. The carrier effect which is thus improved makes it possible to increase the efficaceousness of a cosmetic or pharmaceutical composition intended for a topical application, in which the cosmetically or pharmaceutically active compound is contained in the vesicles.

The dispersion according to the invention may thus contain at least one cosmetically or pharmaceutically active compound, either in the encapsulated aqueous phase of the vesicles if the said active material is water-soluble, or in the lipid phase of the vesicles if it is oil-soluble if the active material is amphiphilic, it then distributes itself between the lipid phase arid the encapsulated aqueous phase of each vesicle, according to its partition coefficient. According to the invention a cosmetically or pharmaceutically active compound may also be present in the aqueous medium of the dispersion.

The various active substances which may be present in the vesicles or in the aqueous medium of the dispersion according to the invention, regardless of whether they are hydrophilic, lipophilic or amphiphilic, are especially those described in Table I of FR-A-2694884.

The aqueous medium of the dispersion according to the invention may additionally contain conventional additives employed for the formulation of the dispersion in the form of lotion, cream or serum. In particular, these adjuvants are taken from the group made up of gelling agents, stabilizers, colorants, opacifiers and perfumes. Among the gelling agents that can be employed there may be mentioned cellulose derivatives such as hydroxyethyl cellulose, derivatives of algae, such as satiagum, natural gums such as tragacanth and synthetic polymers, in particular the mixtures of polycarboxyvinyl acids marketed under the name "Carbopol®" by Goodrich and the mixture of Na acrylate/acrylamide copolymers marketed under the name "Hostacerin PN73®" by Hoechst.

The dispersion according to the invention can also be employed for dispersing oils. Oils which may be mentioned are, for example, oils of vegetable origin, mineral oils, synthetic oils and silicone oils.

Another subject-matter of the present invention is therefore a cosmetic or pharmaceutical composition for topical application, characterized in that it consists essentially of a dispersion according to the invention, in which the vesicles contain at least one cosmetically or pharmaceutically active compound.

Topical application is understood according to the invention to mean a local application of the composition to the skin, the exoskeletal parts, the mucosae or the hair.

The cosmetic or pharmaceutical compositions according to the invention have been found to offer a very particular advantage on application to the skin, including the scalp. They promote skin care and especially hydration, nutrition, protection and firming up. Depending on the active material (s) employed, they have furthermore an antiage, antiwrinkle, slimming, depigmenting and actiacne effect and promote the treatments of mycosis, of dermatitis and of psoriasis. They can also be employed as compositions for skin make-up.

Another subject-matter of the present invention is therefore the use of a composition as defined above for the care and/or make up of the skin or for the care of the scalp and/or hair.

In addition, a subject-matter of the present invention is a process for nontherapeutic treatment of the skin or of the scalp, characterized in that it consists in applying to the skin or to the scalp a composition as defined above.

Examples of preparation of a dispersion according to the invention and of compositions obtained from such a dispersion will now be given by way of illustration.

In what follows, the proportions of the various components are expressed as weight percentage relative to the total weight of the final dispersion according to the invention.

EXAMPLE 1

Preparation of a Dispersion According to the Invention

A lipid phase consisting of the following components:
Polyethylene glycol 400 stearate (marketed by Unichema) . . . 1.9%
Cholesterol . . . 1.9%
"Acylglutamate HS 11®" (monosodium salt of N-Stearoylglutamic acid, marketed by Ajinomoto) . . . 0.2% is heated to a temperature of 110° C. with stirring in order to produce a preassociation by combined melting of the lipids and the mixture thus obtained is then brought to ambient temperature.

The lipid phase thus obtained is then introduced (second alternative form) with rapid stirring (bar magnet/Moritz) into a polymer dispersion in the form of particles, maintained at a temperature of 80° C. and which has the following composition:

Polyester containing sulphonic groups "AQ38®" (marketed by Eastman Chemical; mean particle size of between 5 and 60 nm) . . . 0.4%
Demineralized water q.s. . . . 100%

Stirring is allowed to continue for one hour. The dispersion is then passed, with two repeats, through a high-pressure homogenizer at 500 bars at ambient temperature. The mean size of the vesicles is finally of the order of 200 nm.

The dispersion according to the invention thus obtained is subjected to a freeze-drying operation to test, in an extreme manner, the dehydration resistance of the vesicles, as described above.

After rehydration with demineralized water it is found, on the one hand, that there is no recrystallization of lipid and that the dispersion is fine and homogeneous and, on the other hand, that the mean size of the vesicles is smaller than twice the initial mean size of the vesicles; the freeze-drying test is therefore found to be positive.

The same result in the freeze-drying test is obtained by mixing the polymer in dispersion as described above with an aqueous dispersion of vesicles which has already been formed from demineralized water and from the lipid phase also described above (first alternative form), by employing the same proportions of each component relative to the total weight of the final dispersion.

Dispersions of the same type as those obtained above were produced according to an identical procedure but employing other substances for forming the lipid phase and various types of polymers for forming the dispersion. Among the latter there may be mentioned in particular polyesters containing sulphonic groups, such as those marketed under the names "AQ 29®", "AQ 1350®", "AQ 1950®" and AQ 14000®" by Eastman Chemical and those marketed under the names of "Polycare®" by Rhône-Poulenc.

EXAMPLE 2

Antiage Serum Composition for the Face

A dispersion according to the invention is produced as described in Example 1 by incorporating, when the vesicles are being formed, the classical active principles of an antiage serum, to obtain the following composition:
Lipid Phase:
Polyethylene glycol 400 stearate . . . 1.425%
Cholesterol . . . 1.425%
"Acylglutamate HS 11®" . . . 0.15%
Polymer in Dispersion:
Polyester containing sulphonic groups "AQ38®" . . . 0.3%
Glycerol . . . 3%
L-Hydroxyproline . . . 1%
D-Panthenol . . . 1.5%
Guanosine . . . 0.01%
T-Lysine monohydrate q.s. pH=6.5
Demineralized water q.s. 100 g After the dispersion has been formed, 0.3% of a gelling agent (mixture of polycarboxyvinyl acids: "Carbopol 940®" marketed by Goodrich) is added to it.

In this example the active principles of the composition may be advantageously replaced with other active principles for the care or the treatment of the skin, such as, for example, antiwrinkle or antiacne active substances or substances with a slimming action.

I claim:

1. A dispersion, in an aqueous medium, of dehydration-resistant vesicles consisting of a lipid phase and of an encapsulated aqueous phase, wherein said dispersion additionally contains, either in the said aqueous medium or in the said encapsulated aqueous phase, or in both at the same time, at least one polymer in dispersion in the form of particles, said polymer having a glass transition temperature Tg, in the presence or absence of a plasticizing agent, lower than 70° C. at 0% relative humidity or lower than 55° C. at 65% relative humidity.

2. The dispersion according to claim 1, wherein said polymer is a synthetic polymer.

3. The dispersion according to claim 2, wherein said synthetic polymer is selected from the group consisting of polyesters, polyurethanes, polymers containing carboxylic acid functional groups, and vinyl polymers.

4. The dispersion according to claim 1, wherein the said polymer includes a plasticizing agent.

5. The dispersion according to claim 4, wherein the said plasticizing agent is selected from the group consisting of dipropylene glycol methyl ether, tripropylene glycol methyl ether, diethyl adipate, diisopropyl adipate and glycerol triacetate.

6. The dispersion according claim 1, wherein the said polymer in dispersion is such that the mean size of the particles of the said polymer is between 5 and 200 nm.

7. The dispersion according to claim 1, wherein the mean size of the vesicles is between 10 and 5000 nm.

8. The dispersion according to claim 1, wherein the concentration of the said polymer in dispersion is between 0.01 and 30% of the said polymer relative to the total weight of the dispersion.

9. The dispersion according to claim 1, wherein the vesicle concentration is between 0.1 and 30% by weight of the said lipid phase relative to the total weight of the dispersion.

10. The dispersion according to claim 1, wherein the weight ratio of the said polymer to the said lipid phase is between 1:500 and 20:1.

11. The dispersion according to claim 10, wherein the said weight ratio is between 1:100 and 1:1.

12. A cosmetic or pharmaceutical composition for topical application, which consists essentially of a dispersion according to claim 1, in which the vesicles contain at least one cosmetically or pharmaceutically active compound.

13. A process for the treatment of the skin or of the scalp, which consists in applying to the skin or to the scalp a cosmetic composition according to claim 12.

14. The dispersion of claim 1, wherein said polymer is a polymer of natural origin.

15. The dispersion of claim 14, wherein said polymer of natural origin is selected from the group consisting of shellac resin, sandarac gum, dammars, elemis, copals, cellulose derivatives, and mixtures thereof.

16. A dispersion, in an aqueous medium, of dehydration-resistant vesicles consisting of a lipid phase and of an encapsulated aqueous phase, wherein said dispersion additionally contains, either in the said aqueous medium or in the said encapsulated aqueous phase, or in both at the same time, at least one polymer in dispersion in the form of particles, said polymer having a glass transition temperature Tg, in the presence or absence of a plasticizing agent, lower than 70° C. at 0% relative humidity or lower than 55° C. at 65% relative humidity, said polymer being a polyester selected from the group consisting of polyesters containing sulphonic groups, polyesters containing sulphonic groups additionally containing units derived from ethylene glycol, from tri- and tetraethylene glycol and from terephthalate, neutralized polyesters containing a terminal amine functional group, polyester block copolymers of phthalic and sulphonphthalic acid/ethylene glycol/polymethyl siloxane α,γ-hydroxypropyl and vinyl acetate/vinyl butylbenzoate/crotonic acid copolymers.

17. The dispersion of claim 16, wherein said particles have a mean size of between 5 and 200 nm.

18. The dispersion of claim 16 wherein said vesicles have a mean size of between 10 and 5000 nm.

19. The dispersion of claim 16 wherein the concentration of said polymer in dispersion is between 0.01 and 30% of said polymer relative to the total weight of the dispersion.

20. The dispersion of claim 16 wherein the vesicle concentration is between 0.1 and 30% by weight of the lipid phase relative to the total weight of the dispersion.

21. The dispersion of claim 16 wherein the weight ratio of the polymer to the lipid phase is between 1:500 and 20:1.

22. The dispersion according to claim 21 wherein the weight ratio is 1:100 and 1:1.

23. A cosmetic or pharmaceutical composition for topical application which consists essentially of a dispersion of claim 16 in which the vesicles contain at least one cosmetically or pharmaceutically active compound.

24. A process for treatment of the skin or scalp consisting of applying to the skin or scalp a cosmetic composition according to claim 23.

\* \* \* \* \*